US005741928A

United States Patent [19]
Kobayashi et al.

[11] Patent Number: 5,741,928
[45] Date of Patent: Apr. 21, 1998

[54] PROCESS FOR PRODUCING BIS (AMINOMETHYL) CYCLOHEXANE

[75] Inventors: Shoichi Kobayashi; Susumu Naito, both of Niigata-ken, Japan

[73] Assignee: Mitsubishi Gas Chemical Company, Inc., Tokyo, Japan

[21] Appl. No.: 540,026

[22] Filed: Sep. 19, 1995

[30] Foreign Application Priority Data

Sep. 21, 1994 [JP] Japan .................. 6-226740

[51] Int. Cl.$^6$ .................. C07C 219/72; C07C 211/18
[52] U.S. Cl. .................. 564/449; 564/461; 564/462; 564/451
[58] Field of Search .................. 564/450, 451, 564/461, 462, 449

[56] References Cited

U.S. PATENT DOCUMENTS

| | | | |
|---|---|---|---|
| 3,959,374 | 5/1976 | Brennan et al. | 564/449 |
| 5,371,293 | 12/1994 | Takagawa et al. | 564/449 |

FOREIGN PATENT DOCUMENTS

| | | |
|---|---|---|
| 21 61 169 | 7/1972 | Germany. |
| 25 11 280 A1 | 9/1975 | Germany. |
| 30 03 731 A1 | 8/1980 | Germany. |
| 42-26783 | 12/1967 | Japan. |
| 50-126638 | 10/1975 | Japan. |
| 51-7659 | 3/1976 | Japan. |
| 53-79840 | 7/1978 | Japan. |
| 61-13461 | 4/1986 | Japan. |

OTHER PUBLICATIONS

Patent Abstracts of Japan; vol. 3, No. 043 (C–042) 13 Apr. 1979; JP-A-54 016452 (Takeda Yakuhin Kogyo K.K.), Abstract.
Patent Abstracts of Japan; vol. 2, No. 117 (C023), 29 Sep. 1978; JP-A-53 079840 (Takeda Yakuhin Kogyo K.K.), Abstract.
Database WPI, Week 6800; Derwent Publications Ltd., London, GB; JP-A-42 026 783 (Toyo Rayon Co., Ltd), Abstract (Dec. 1967).

*Primary Examiner*—José G. Dees
*Assistant Examiner*—Barbara Badio
*Attorney, Agent, or Firm*—Armstrong, Westerman Hattori, McLeland & Naughton

[57] ABSTRACT

Disclosed is a process for producing bis(aminomethyl) cyclohexane, which comprises hydrogenating a xylylenediamine in the presence of a catalyst and at least one solvent selected from the group consisting alkylamines and alkylenediamines.

8 Claims, No Drawings

5,741,928

1

PROCESS FOR PRODUCING BIS (AMINOMETHYL) CYCLOHEXANE

BACKGROUND OF THE INVENTION

1) Field of the Invention

The present invention relates to a process for producing bis(aminomethyl)cyclohexane from xylylenediamine.

Bis(aminomethyl)cyclohexane is an industrially important compound as a raw material for polyamides, bis (isocyanatomethyl)cyclohexane, etc.

2) Prior Art

Bis(aminomethyl)cyclohexane can be obtained by catalytic hydrogenation treatment for xylylenediamine. As conventional processes of catalytic hydrogenation for xylylenediamine, the following processes are known.

Japanese Patent Publication No. 42-26783 discloses a process for producing cis-bis(aminomethly)cyclohexane by catalytic hydrogenation for xylylenediamine in the presence of a rhodium catalyst and water or organic acid-containing water as a solvent. When water is used as a solvent, the yield of cis-bis(aminomethyl)cyclohexane is low. Further, when organic acid-containing water is used as a solvent, the operation is complicated because it is necessary that after catalytic hydrogenation the reaction liquid is filtered to remove the catalyst and then the solvent is distilled off and further an alkali is added to the residue to deposit free amines and then vacuum distillation is carried out to obtain cis-bis(aminomethyl)cyclohexane. Also in the case, the yield of cis-bis(aminomethyl)cyclohexane (methylamine) is not always satisfied.

Japanese Patent Kokai (Laid open) No. 50-126638 discloses a process for producing bis(aminomethyl) cyclohexane by catalytic hydrogenation for xylylenediamine in the presence of a ruthenium catalyst in the absence of a solvent or in the presence of an organic solvent at about 150° C. in a liquid phase. The process provides a large amount of by-products and low yields for intended bis(aminomethyl) cyclohexane because the reaction temperature is as considerably high as about 150° C.

Japanese Patent Publication NO. 51-7659 discloses a process for producing bis(aminomethyl)cyclohexane by catalytic hydrogenation for xylylenediamine in the presence of a ruthenium catalyst and liquid ammonia. In the process, it is necessary to maintain a high pressure because liquid ammonia is used and to provide a high pressure recovering equipment and a high pressure refrigerating equipment because liquid ammonia is recycled to use again and further a high cost of equipment is required because measures against odor and air pollution including installation of draft, fan, combustion furnace, etc., are necessary as protection for working environment.

Japanese Patent Publication No. 61-13461 discloses a process for producing bis(aminomethyl)cyclohexane by catalytic hydrogenation for xylylenediamine in the presence of a ruthenium catalyst, 6 to 40% by weight of water and an alkaline metal or an alkaline earth metal. In the process, although a yield for bis(aminomethyl)cyclohexane is high, steps including separation by filtration, water separation under low vacuum etc., in order to purify the intended substance from products are required because an alkaline metal or an alkaline earth metal adheres on a surface of the catalyst to deteriorate the catalyst activity. Accordingly, the process is complicated as a continuous production process and not suitable for industrial equipments.

As described above, in processes for producing bis (aminomethyl)cyclohexane by catalytic hydrogenation for

2 xylylenediamine, a ruthenium catalyst or a rhodium catalyst has been used and further processes also wherein various solvents are employed have been suggested. However, in the processes, a satisfactory yield is not always obtained in industrial equipments and from problems including working environment, etc., a high cost of equipment and complicated operation are required. In such present circumstance, improvement for the production process has been required.

SUMMARY OF THE INVENTION

The object of the present invention is to provide a process for producing bis(aminomethyl)cyclohexane from xylylenediamine in a high yield by comparatively simple operation, which causes no problem in working environment and can operated under a lower pressure than that in prior processes.

As a result of an extensive study for the above-mentioned subjects in producing bis(aminomethyl)cyclohexane by catalytic hydrogenation for xylylenediamine, the present inventors have found that bis(aminomethyl)cyclohexane can be produced in a high yield and in a comparatively simple operation and under a lower pressure than that in prior processes without causing problem in working environment by catalytic hydrogenation for xylylenediamine in the presence of a catalyst and at least one solvent selected from the group consisting of alkylamines and alkylenediamines, and have established the present invention.

That is, the present invention provides a process for producing bis(aminomethyl)cyclohexane, which comprises hydrogenating a xylylenediamine in the presence of a catalyst and at least one solvent selected from the group consisting of alkylamines and alkylenediamines.

Further, as a preferred embodiment, the present invention includes also a process for producing bis(aminomethyl) cyclohexane wherein bis(aminomethyl)cyclohexane obtained by the hydrogenation in the presence of a ruthenium catalyst is recycled to use as a solvent in the catalytic hydrogenation.

DETAILED DESCRIPTION OF THE INVENTION

The present invention will be described in detail below.

Xylylenediamine as a raw material in the present invention has three species of isomers, i.e., ortho-, meta- and para-isomers. Ortho-, meta- or para-xylylenediamine each is used alone or in a mixture thereof as a raw material. Particularly, the process according to the present invention is suitable to hydrogenation for meta- and para-xylylenediamines.

The catalyst for catalytic hydrogenation being used the present invention is not limited. Examples include a ruthenium catalyst, a rhodium catalyst, a nickel catalyst and a combination thereof. Particularly, a ruthenium catalyst is preferable. Examples of a ruthenium catalyst include ruthenium metal, ruthenium oxide, ruthenium hydroxide, etc. It is preferred to use the catalyst supported on alumina, diatomaceous earth, carbon, etc.

The amount of the catalyst being supported depends on species and shapes of catalyst, species of raw material of the catalyst, reaction temperature, feeding amount of hydrogen, etc. For example, when alumina is used as a carrier, about 2% by weight of ruthenium is supported on granula alumina having 1 to 2 mmø. The thus supported ruthenium catalyst is charged into a reactor to use as a fixed bed.

Alkylamines and alkylenediamines being used as a solvent in the present invention are separated from reaction products by distillation to recycle. In order to make recycling easy in an industrial continuous production process, alkylamines and alkylenediamines being a liquid at an ordinary temperature and having carbon atoms 1 to 18 are selected, which are effective in reducing by-products and improving a yield of bis(aminomethyl)cyclohexane.

Examples of alkylamines include methylamine, dimethylamine, trimethylamine, ethylamine, diethylamine, triethylamine, propylamine, dipropylamine, isopropylamine, diisopropylamine, butylamine, dibutylamine, tributylamine, hexylamine, cyclohexylamine, 2-ethylhexylamine, etc.

Examples of alkylenediamines include ethylenediamine, propylenediamine, 1,4-butylenediamine, hexamethylenediamine, bis(aminomethyl)cyclohexane, etc.

Among them, particularly, bis(aminomethyl)cyclohexane is advantageous in the process because bis(aminomethyl) cyclohexane obtained by catalytic hydrogenation can be recycled.

In the present invention, at least one solvent selected from the group consisting of alkylamines and alkylenediamines is used.

The ratio by weight of the above-mentioned solvent to xylylenediamine as a raw material is 1:30 to 1:1, preferably 1:20 to 1:3.

The above-mentioned solvent may be used in a mixture of other organic solvents.

Examples of the organic solvents being used include alcohols including methanol, ethanol, isopropylalcohol, n-propylalcohol, etc.

The hydrogen pressure being applied in catalytic hydrogenation is 5 kg/cm$^2$G or above. Industrially, it is preferred to be 50 to 150 kg/cm$^2$G. It is possible to carry out the process according to the present invention also under a lower pressure than that in conventional processes.

The reaction temperature is 50° to 150° C., preferably 80° to 130° C.

The amount of the catalyst being used in the present invention, in case of using the above-mentioned catalyst supported about 2% by weight of ruthenium, is 0.3 to 5.0 g/g·hr as WHSV (feeding rate of xylylenediamine per weight of catalyst), preferably 0.5 to 2.0.

Bis(aminomethyl)cyclohexane as intended product is easily separated from the reaction products by distilling off alkylamines, alkylenediamines and organic solvents under atmospheric pressure and then vacuum distilling.

The process according to the present invention can be carried out either batchwise or in a continuous process. In a continuous process, solvent-containing reaction products withdrawn from a reactor are transferred to a vapor-liquid separator to separate dissolved gases being used as a fuel. Then, the solvent-containing reaction products thus separated dissolved gases are transferred to solvent recovery facility to recover the solvent from the solvent-containing reaction product. The thus recovered solvent is recycled to the reactor. The reaction products are transferred to a product purifying facility to obtain purified bis(aminomethyl) cyclohexane. When bis(aminomethyl)cyclohexane is used as a solvent in the process according to the present invention, bis(aminomethyl)cyclohexane as a product in which dissolved gases has been separated in the vapor-liquid separator is recycled directly to the reactor without being transferred to the solvent recovery facility.

PREFERRED EMBODIMENT OF THE INVENTION

The present invention will be described in detail below, referring to Examples, which are not limitative of the present invention.

In all Examples and Comparative Examples, a flow type and exterior heating type of a fixed bed-reactor having inner diameter 10 mmø and length 450 mm was used.

EXAMPLE 1

25 g of a granular catalyst (1 to 2 mmø, 25 ml) 2 wt. % of ruthenium supported on alumina, which was available on the market, was used.

36.4 g/hr of a mixture being composed of metaxylylenediamine 15 wt. % as a raw material and 1,3-bis (aminomethyl)cyclohexane 85 wt. % as a solvent was fed to the reactor at a reaction temperature of 120° C. under a reaction pressure of 100 kg/cm$^2$G at a hydrogen gas space velocity (GSV) of 400 hr$^{-1}$.

The reaction products were collected over one hour in 24 hours after the reaction has started to analyze by gaschromatography. As a result, it was found that the yield of 1,3-bis(aminomethyl)cyclohexane containing no initial amount of 1,3-bis(aminomethyl)cyclohexane as a solvent was 94.0 mol %, and as other products 0.4 mol % of metaxylene, 2.7 mol % of 3-aminomethyl-1-methylcyclohexane, 2.5 mol % of 3-methylbenzylamine and 0.4 mol % of unreacted metaxylylenediamine were obtained.

COMPARATIVE EXAMPLE 1

The hydrogenation reaction was carried out in the same manner as in Example 1 except that 24.6 g/hr of a mixture being composed of metaxylylenediamine 15 wt. % as a raw material and liquid ammonia 85 wt. % as a solvent was bed to the reactor under a reaction pressure of 103 kg/cm$^2$G.

As a result of analysis by gaschromatography, it was found that the yield of 1,3-bis(aminomethyl)cyclohexane was 93.1 mol %, and as other products 0.1 mol % of metaxylene, 6.1 mol % of 3-aminomethyl-1-methylcyclohexane, 0.2 mol % of 3-methylbenzylamine and 0.2 mol % of unreacted metaxylylenediamine were obtained.

EXAMPLE 2

The hydrogenation reaction was carried out in the same manner as in Example 1 except that 24.4 g/hr of a mixture being composed of metaxylylenediamine 10 wt. % as a raw material and 1,3-bis(aminomethyl) cyclohexanediethylamine 90 wt. % as a solvent was fed to the reactor under a reaction pressure of 52 kg/cm$^2$G at a reaction temperature of 115° C.

As a result of analysis by gaschromatography, it was found that the yield of 1,3-bis(aminomethyl)cyclohexane was 94.0 mol %, and as other products 0.5 mol % of metaxylene, 3.7 mol % of 3-aminomethyl-1-methylcyclohexane, 1.7 mol % of 3-methylbenzylamine and 0.1 mol % of unreacted metaxylylenediamine were obtained.

COMPARATIVE EXAMPLE 2

The hydrogenation reaction was carried out in the same manner as in Example 1 except that 32.5 g/hr of a mixture being composed of metaxylylenediamine 8 wt. % as a raw material and liquid ammonia 92 wt. % as a solvent was fed to the reactor under a reaction pressure of 50 kg/cm$^2$G at a reaction temperature of 115° C.

As a result of analysis by gaschromatography, it was found the yield of 1,3-bis(aminomethyl)cyclohexane was 33.3 mol % and as other products 0.3 mol % of metaxylene, 0.6 mol % of 3-aminomethyl-1-methylcyclohexane, 4.7 mol of 3-methylbenzylamine and 61.1 mol % of unreacted metaxylylenediamine were obtained.

EXAMPLE 3

The hydrogenation reaction was carried out in the same manner as in Example 1 except that 27.6 g/hr of a mixture being composed of metaxylylenediamine 15 wt. % as a raw material and diethylamine 85 wt. % as a solvent was led to the reactor.

As a result of analysis by gaschromatography, it was found that the yield of 1,3-bis(aminomethyl)cyclohexane was 95.0 mol %, and as other products 3.9 mol % of 3-aminomethyl-1-methylcyclohexane, 0.9 mol % of 3-methylbenzylamine and 0.2 mol % of metaxylene were obtained.

EXAMPLE 4

The hydrogenation reaction was carried out in the same manner as in Example 1 except that 28.1 g/hr of a mixture being composed of metaxylylenediamine 15 wt. % as a raw material and triethylamine 85 wt. % as a solvent was fed to the reactor.

As a result of analysis by gaschromatography, it was found that the yield of 1,3-bis(aminomethyl)cyclohexane was 93.8 mol %, and as other products 4.6 mol % of 3-aminomethyl-1-methylcyclohexane, 1.4 mol % of 3-methylbenzylamine and 0.2 mol % of metaxylene were obtained.

EXAMPLE 5

The hydrogenation reaction was carried out in the same manner as in Example 1 except that 27.9 g/hr of a mixture being composed of metaxylylenediamine 15 wt. % as a raw material and isopropylamine 85 wt. % as a solvent was fed to the reactor.

As a result of analysis by gaschromatography, it was found that the yield of 1,3-bis(aminomethyl)cyclohexane was 94.3 mol %, and as other products 4.3 mol % of 3-aminomethyl-1-methylcyclohexane, 1.2 mol % 3-methylbenzylamine and 0.2 mol % of metaxylene were obtained.

EXAMPLE 6

The hydrogenation reaction was carried out in the same manner as in Example 1 except that 28.4 g/hr of a mixture being composed of metaxylylenediamine 15 wt. % as a raw material and diethylamine 42.5 wt % and methanol 42.5 wt. % as a solvent was fed to the reactor.

As a result of analysis by gaschromatography, it was found that the yield of 1,3-bis(aminomethyl)cyclohexane was 94.1 mol %, and as other products 3.7 mol % of 3-aminomethyl-1-methylcyclohexane, 2.0 mol % of 3-methylbenzylamine and 0.2 mol % of metaxylene were obtained.

EXAMPLE 7

The hydrogenation reaction was carried out in the same manner as in Example 1 except that 27.3 g/hr of a mixture being composed of paraxylylenediamine 15 wt % as a raw material and diethylamine 42.5 wt. % as a solvent was fed to the reactor.

As a result of analysis by gaschromatography, it was found that the yield of 1,4-bis(aminomethyl)cyclohexane was 95.9 mol % and as other products 3.4 mol % of 4-aminomethyl-1-methylcyclohexane, 0.3 mol % of 4-methyl-benzylamine and 0.2 mol % of paraxylene were obtained.

EXAMPLE 8

The hydrogenation reaction was carried out in the same manner as in Example 1 except that 35.0 g/hr of a mixture being composed of metaxylylenediamine 15 wt. % as a raw material and ethylenediamine 85 wt. % as a solvent was fed to the reactor.

As a result of analysis by gaschromatography, it was found that the yield of 1,3-bis(aminomethyl)cyclohexane was 91.5 mol %, and as other products 0.6 mol % of 3-aminomethyl-1-methylcyclohexane, 4.6 mol % of 3-methylbenzylamine, 0.2 mol % of metaxylene and 3.1 mol % of unreacted metaxylylenediamine were obtained.

COMPARATIVE EXAMPLE 3

The hydrogenation reaction was carried out in the same manner as in Example 1 except that 24.6 g/hr of a mixture being composed of metaxylylenediamine 15 wt. % as a raw material and water 85 wt. % as a solvent was fed to the reactor.

As a result of analysis by gaschromatography, it was found that the yield of 1,3-bis(aminomethyl)cyclohexane was 87.9 mol %, and as other products 8.4 mol % of 3-aminomethyl-1-methylcyclohexane, 2.8 mol % of 3-methylbenzylamine and 0.4 mol % of metaxylene were obtained.

As clear from Examples, 1,3-bis(aminomethyl) cyclohexane can be obtained in a high yield by using alkylamines or alkylenediamines in the present invention as a solvent. Although it has been regarded that prior process for using liquid ammonia is industrially the most advantageous, it is necessary to maintain a reaction pressure to about 100 kg/cm$^2$ and to provide a high pressure recovery equipment and a high pressure refrigerating equipment because liquid ammonia is recycled to use again, and further measures against odor and air pollution including installation of draft, fan, combustion furnace, etc., are required as protection for working environment.

In Comparative Example 2 wherein liquid ammonia was used as a solvent and the reaction pressure was lowered to 50 kg/cm$^2$G, the yield of bis(aminomethyl)cyclohexane remarkably decreased since a portion of liquid ammonia was vaporized in the reactor temperature. In contrast, as shown in Example 2 according to the present invention, bis (aminomethyl)cyclohexane was obtained in a high yield even under a low pressure.

According to the present invention, bis(aminomethyl) cyclohexane can be obtained in a high yield and a small amount of by-product at a high reaction velocity even under comparatively mild conditions of a low pressure by catalytic hydrogenation for xylylenediamine.

The process according to the present invention cause no problems in working environment, and can be readily conducted. Thus, the process is industrially very advantageous because alkylamines and alkylenediamines being used in the present invention are easily separated from reaction products by distillation and recycled to use again.

Furthermore, in the process according to the present invention, bis(aminomethyl)cyclohexane can be industrially very advantageously produced by simple distillation operation and simple separation operation because bis (aminomethyl)cyclohexane as a reaction product can be recycled to use again.

What is claimed is:

1. A process for producing bis(aminomethyl)cyclohexane, which comprises hydrogenating a xylylenediamine in the presence of a catalyst and at least one solvent selected from the group consisting of alkylamines having 1 to 18 carbon atoms and alkylenediamines having 1 to 18 carbon atoms, and wherein said hydrogenating is carried out at a pressure of from 5 to 150 kg/cm$^2$G.

2. A process according to claim 1, wherein a ratio by weight of the solvent to xylylenediamine is 1:30 to 1:1.

3. A process according to claim 1, wherein the solvent further contains an alcohol.

4. A process according to claim 1, wherein bis (aminomethyl)cyclohexane obtained by the hydrogenation is recycled to use as the solvent.

5. A process according to claim 1, wherein the catalyst is a ruthenium catalyst.

6. A process for producing bis (aminomethyl) cyclohexane, which comprises hydrogenating, in the absence of ammonia, a xylylenediamine in the presence of a catalyst and at least one solvent selected from the group consisting of alkylamines and alkylenediamines.

7. A process according to claim 6, wherein the alkylenediamines or alkylamines have 1 to 18 carbon atoms.

8. A process according to claim 6, wherein the hydrogenation is carried out under a pressure of 5 to 150 kg/cm$^2$G.

* * * * *